United States Patent
Drozdzak

(10) Patent No.: US 8,519,069 B2
(45) Date of Patent: Aug. 27, 2013

(54) CATALYTIC COMPLEX FOR OLEFIN METATHESIS REACTIONS, PROCESS FOR THE PREPARATION THEREOF AND USE THEREOF

(75) Inventor: Renata Drozdzak, Drocourt (FR)

(73) Assignee: RIMTEC Corporation, Tokyo (JP)

( * ) Notice: Subject to any disclaimer, the term of this patent is extended or adjusted under 35 U.S.C. 154(b) by 0 days.

(21) Appl. No.: 13/384,957

(22) PCT Filed: Jul. 7, 2010

(86) PCT No.: PCT/EP2010/059719
§ 371 (c)(1),
(2), (4) Date: Jan. 19, 2012

(87) PCT Pub. No.: WO2011/009721
PCT Pub. Date: Jan. 27, 2011

(65) Prior Publication Data
US 2012/0271019 A1 Oct. 25, 2012

(30) Foreign Application Priority Data
Jul. 21, 2009 (EP) .................................... 09290578

(51) Int. Cl.
*C08G 61/08* (2006.01)
*C07F 15/00* (2006.01)
*C07C 6/06* (2006.01)
*C08F 4/80* (2006.01)

(52) U.S. Cl.
USPC ........... 526/171; 502/155; 526/129; 526/283; 526/904; 548/103; 556/22; 556/137; 585/645

(58) Field of Classification Search
USPC .................. 548/103; 556/22, 137; 526/171, 526/129, 283; 585/645; 502/155
See application file for complete search history.

(56) References Cited

U.S. PATENT DOCUMENTS
2008/0293905 A9* 11/2008 Schaubroeck et al. ........ 526/283

FOREIGN PATENT DOCUMENTS
| EP | 1 577 282 A2 | 9/2005 |
| EP | 1 757 613 A1 | 2/2007 |
| EP | 2 151 445 A1 | 2/2010 |
| EP | 2 151 446 A1 | 2/2010 |
| WO | 99/22865 A1 | 5/1999 |
| WO | 00/15339 A1 | 3/2000 |
| WO | 03/062253 A1 | 7/2003 |

OTHER PUBLICATIONS

P.A. Van der Schaaf et al., "Synthesis and reactivity of novel ruthenium carbene catalysts", J. Organomet. Chem., vol. 606, pp. 65-74 (2000).
T. Ung et al., "Latent Ruthenium Olefin Metathesis Catalysts that Contain an N-Heterocyclic Carbene Ligand", Organometallics, vol. 23, pp. 5399-5401 (2004).
B. Allaert et al., "Synthesis and activity for ROMP of bidentate Schiff base substituted second generation Grubbs catalysts", J. Mol. Cat. A: Chem., vol. 260, pp. 221-226 (2006).
B. De Clercq et al., "Activity of a new class of ruthenium based ring-closing metathesis and ring-opening metathesis polymerization catalysts coordinated with a 1,3-dimesityl-4,5-dihydroimidazol-2-ylidene and a Schiff base ligand", Tetrahedron Lett., vol. 43, pp. 9101-9104 (2002).
N. Ledoux et al., "In situ generation of highly active olefin metathesis initiators", J. Organomet Chem., vol. 691, pp. 5482-5486 (2006).
K. Keitz et al., "A Tandem Approach to Photoactivated Olefin Metathesis: Combining a Photoacid Generator with an Acid Activated Catalyst", J. Am. Chem. Soc., vol. 131, pp. 2038-2039 (2009).
English Abstract for EP 1 468 004, Corresponds to WO 03062253, Universiteit Gent (Oct. 20, 2004).

* cited by examiner

*Primary Examiner* — Fred M Teskin
(74) *Attorney, Agent, or Firm* — Edwards Wildman Palmer LLP; Peter F. Corless; Christine C. O'Day

(57) ABSTRACT

The present invention relates to a catalytic complex for olefin metathesis reactions, to a process for its preparation and to its use in olefin metathesis reactions, particularly in ring opening metathesis polymerisation (ROMP) reactions.

18 Claims, No Drawings

CATALYTIC COMPLEX FOR OLEFIN METATHESIS REACTIONS, PROCESS FOR THE PREPARATION THEREOF AND USE THEREOF

FIELD OF THE INVENTION

The present invention relates to a catalytic complex for olefin metathesis reactions, to a process for its preparation and to its use in olefin metathesis reactions, particularly in ring opening metathesis polymerisation (ROMP) reactions.

BACKGROUND OF THE INVENTION

During recent years, olefin metathesis has seen an extraordinary development and has turned out to be a very versatile and efficient tool in organic synthesis.

The success of the olefin metathesis reaction is mainly attributed to the versatility and the development of well-defined Ruthenium catalysts stable to demanding reaction conditions. As these catalysts became commercially available and were exposed to a myriad of potentially interesting applications, the field was faced with renewed challenges, e.g. catalyst latency. The ideal latent olefin metathesis catalyst exhibits no catalytic activity in the presence of monomer or substrate at room temperature, but can be triggered quantitatively to a highly active form by thermal, chemical or photochemical activation to initiate the metathesis reaction. Additionally, catalyst stability towards decomposition or thermal degradation should be guaranteed by the rigorous choice of ligand environment.

Industrial application in DCPD polymerization requires the latent catalysts exhibiting decreased initiation rates, which can allow for longer handling of a monomer-catalyst mixture before the polymerization starts.

Van der Schaaf and co-workers developed the temperature activated, slow initiating olefin metathesis catalyst $(PR_3)(Cl)_2Ru(CH(CH_2)_2—C,N-2-C_5H_4N)$ (Scheme 1) in which initiation temperatures were tuned by changing the substitution pattern of the pyridine ring (Van der Schaaf, P. A.; Kolly, R.; Kirner, H.-J.; Rime, F.; Mühlebach, A.; Hefner, A. *J. Organomet. Chem.* 2000, 606, 65-74). Unfortunately, activities of the reported complexes were undesirably low; restricted to 12000 equiv DCPD. Later, Ung reported on analogous tuneable catalytic systems obtained by partially isomerising trans-$(SIMes)(Cl)_2Ru(CH(CH_2)_2—C,N-2-C_5H_4N)$ (2) into the cis analogue (, T.; Hejl, A.; Grubbs, R. H.; Schrodi, Y. *Organometallics* 2004, 23, 5399-5401). However, none of these catalysts allowed for storage in DCPD monomer for long time as the ROMP of DCPD is completed in 25 minutes after catalyst introduction.

Scheme 1

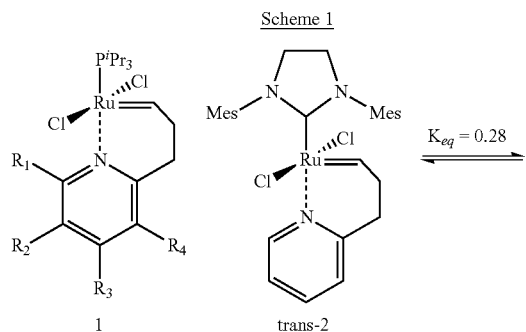

1  trans-2

-continued

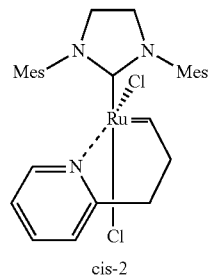

cis-2

In another approach towards rationally designed thermally stable olefin metathesis catalyst for DCPD polymerization, efforts were directed towards the development of an O,N-bidentate Schiff base ligated Ru-carbene catalysts elaborated by Verpoort et al. (Scheme 2, 4, 5, L=SIMes). It was shown that such complexes are extremely inactive at room temperature towards the polymerization of low-strain, cyclic olefins, allow for storage in DCPD for months and can be thermally activated to yield increased activity for the bulk-polymerization of DCPD, but activities comparable to the corresponding complexes without Schiff bases could not be reached (EP 1 468 004; Allaert, B.; Dieltiens, N.; Ledoux, N.; Vercaemst, C.; Van Der Voort, P.; Stevens, C. V.; Linden, A.; Verpoort, F. *J. Mol. Cat. A: Chem.* 2006, 260, 221-226).

Scheme 2

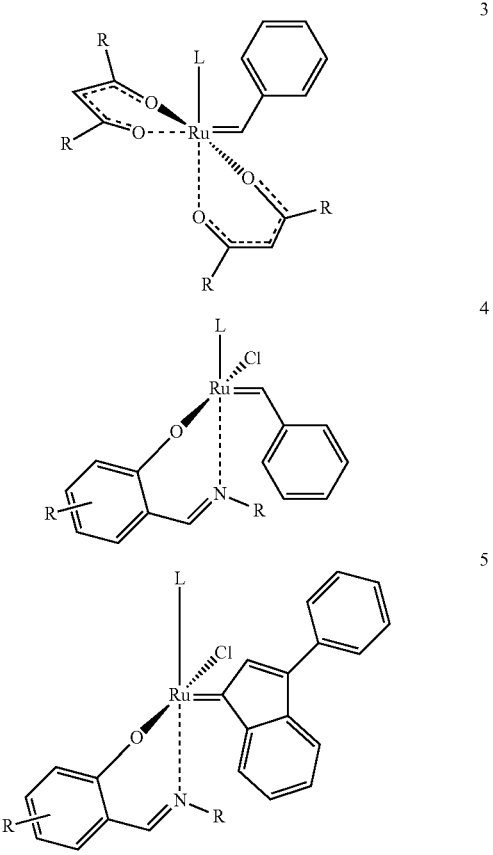

Additionally, activation of the catalyst was facilitated by the addition of high amounts of Bronsted acids (e.g. HCl)

leading to high catalytic activity for the ROMP of DCPD (EP 1 577 282; EP 1 757 613; B. De Clercq, F. Verpoort, *Tetrahedron Lett.*, 2002, 43, 9101-9104; (b) B. Allaert, N. Dieltens, N. Ledoux, C. Vercaemst, Van Der Voort, C. V. Stevens, A. Linden, F. Verpoort, *J. Mol. Catal. A: Chem.*, 2006, 260, 221-226; (c) N. Ledoux, B. Allaert, D. Schaubroeck, S. Monsaert, R. Drozdzak, P. Van Der Voort, F. Verpoort, *J. Organomet. Chem.*, 2006, 691, 5482-5486). However, the requirement of the high amounts of HCl, due its high volatility and corrosion problems prevents them from being industrially applicable.

Recently a series of latent olefin metathesis catalysts bearing 1 bidentate $\kappa^2$-(O,O) ligands were synthesized (Scheme 2, 3). Complex 3, proved to be inactive for the solvent-free polymerization of DCPD. It was furthermore illustrated that complex 3 (Scheme 2, L=PCy$_3$, SIMes) is readily activated upon irradiation of a catalyst/monomer mixture containing a photoacid generator and was found applicable in ROMP of DCPD (D. M. Lynn, E. L. Dias, R. F L Grubbs, B. Mohr, 1999, WO 99/22865). Nevertheless irradiation of a solution of DCPD, 3 (L=SIMes) in a minimal amount of CH$_2$Cl$_2$ resulted in complete gelation within 1 h but solidified and Cross-linked monomer was not obtained. This indicates low catalyst activity and the operation on a low amount of the active species. Moreover the synthetic protocol for catalyst 3 is saddled with a serious drawback, namely the use of a Tl(alkyl-acac). Thallium and its derivatives are extremely toxic; consequently, the use of this procedure is not industrially applicable. In addition, the use of Ag(Me$_6$acac) resulted in complete ligand exchange, but the desired product 3 resisted all attempts at further purification, only ligand exchange using thallium as a more capable transmetalation element provided the desired complex 3 cleanly and in excellent yield (K. Keitz, R. H. Grubbs, *J. Am. Chem. Soc.*, 2009, 131, 2038-2039).

Summarizing, the latent catalysts are of prominent importance for Ring-Opening Metathesis Polymerizations of low-strained cyclic olefins, as they allow for mixing of monomer and catalyst without concomitant gelation or microencapsulation of the precatalyst. Production of a latent catalyst stable in the monomer, highly active after an industrially acceptable activation process and obtained by using environmentally friendly procedure remains challenging.

SUMMARY OF THE INVENTION

It is the object underlying the present invention to provide a catalytic complex for use in olefin metathesis reactions which overcomes the above-mentioned disadvantages of latent Schiff base catalysts and, in particular, to provide a catalyst which is stable in DCPD monomer formulation, easily and efficiently activated by quantitative amounts of a mild Lewis acid, showing exceptional activity after activation and obtained by a simple, efficient, green and highly yielding synthetic process.

This object is solved by a process for the preparation of a catalytic complex consisting of:
a. a metal atom selected from the group consisting of ruthenium and osmium;
b. two bidentate Schiff base ligands comprising an imino group and being coordinated to the metal, in addition to the nitrogen atom of said imino group, through at least one further heteroatom selected from the group consisting of oxygen, sulphur and selenium ligated to said metal;
c. a nucleophilic carbene ligand ligated to said metal; and
d. a carbon-containing ligand ligated to said metal, wherein said carbon-containing ligand is a substituted or unsubstituted alkylidene, vinylidene or indenylidene ligand;
which comprises the step of reacting a ruthenium or osmium catalyst precursor consisting of:
a. a metal atom selected from the group consisting of ruthenium and osmium;
b. two anionic ligands;
c. a nucleophilic carbene ligand ligated to said metal;
d. a carbon-containing ligand ligated to said metal, wherein said carbon-containing ligand is a substituted or unsubstituted alkylidene, vinylidene or indenylidene ligand; and
e. a neutral ligand
or
a ruthenium or osmium catalyst precursor consisting of:
a. a metal atom selected from the group consisting of ruthenium and osmium;
b. one anionic ligand;
c. one bidentate Schiff base ligand comprising an imino group and being coordinated to the metal, in addition to the nitrogen atom of said imino group, through at least one further heteroatom selected from the group consisting of oxygen, sulphur and selenium ligated to said metal;
d. a nucleophilic carbene ligand ligated to said metal; and
e. a carbon-containing ligand ligated to said metal, wherein said carbon-containing ligand is a substituted or unsubstituted alkylidene, vinylidene or indenylidene ligand;
with 1.0 to 3.0 equivalents of a bidentate Schiff base ligand in a non polar solvent and in the presence of a weak base.

Furthermore, the present invention relates to a catalytic complex obtainable by this process, i.e., a catalytic complex consisting of:
a. a metal atom selected from the group consisting of ruthenium and osmium;
b. two bidentate Schiff base ligands comprising an imino group and being coordinated to the metal, in addition to the nitrogen atom of said imino group, through at least one further heteroatom selected from the group consisting of oxygen, sulphur and selenium ligated to said metal;
c. nucleophilic carbene ligand ligated to said metal; and
d. a carbon-containing ligand ligated to said metal, wherein said carbon-containing ligand is substituted or unsubstituted alkylidene, vinylidene or indenylidene ligand.

In addition, the present invention relates to a supported catalyst comprising the above mentioned catalytic complex.

Finally, the present invention relates to the use of the above catalytic complex and supported catalyst in olefin metathesis reactions and, in particular, in ring opening metathesis polymerisation.

Preferred embodiments of the present invention are described in the dependent claims.

DETAILED DESCRIPTION OF THE INVENTION

The catalytic complex according to the present invention comprises a metal atom selected from the group consisting of ruthenium and osmium as the core metal. Preferably, it comprises ruthenium.

In addition, the catalytic complex comprises two bidentate Schiff base ligands comprising an imino group and being coordinated to the metal, in addition to the nitrogen atom of said imino group, through at least one further heteroatom selected from the group consisting of oxygen, sulphur and selenium ligated to said metal. Preferably the heteroatom is oxygen.

Suitable bidentate Schiff base ligands are described, for example, in applicant's European patent 1 468 004. These Schiff base ligands have the general formulae

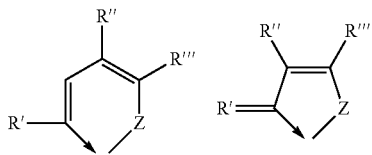

wherein Z is selected from the group consisting of oxygen, sulphur and selenium and wherein R'. R" and R''' are each a radical independently selected from the group consisting of hydrogen, $C_{1-6}$ alkyl, $C_{3-8}$ cycloalkyl, aryl and heteroaryl, or R" and R''' together form an aryl or heteroaryl radical, each said radical being optionally substituted with one or more, preferably 1 to 3, substituents $R_5$ each independently selected from the group consisting of halogen atoms, $C_{1-8}$ alkyl, $C_{1-6}$ alkoxy, aryl, alkyisulfonate, arylsulfonate, alkylphosphonate, arylphosphonate, alkylammonium and arylammonium.

Further, bidentate Schiff base ligands for use in the catalytic complex according to the present invention are disclosed in applicant's co-pending European patent applications EP 08 290 747 and 08 290 748.

These Schiff base ligands are derived from salicylaldimine derivatives of the general formula shown below:

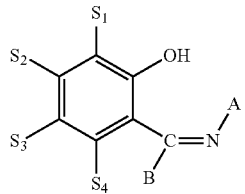

wherein $S_1$ to $S_4$ are substituents which are selected such that the compound has a $pK_a \geq 6.2$ and wherein A is

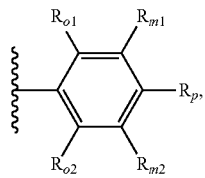

heteroaryl, substituted or unsubstituted alkyl, heteroalkyl or cycloalkyl,

B is hydrogen, $C_1$-$C_{20}$ alkyl, $C_1$-$C_{20}$ heteroalkyl aryl or heteroaryl, wherein each non-hydrogen group may be optionally substituted with one or more moieties selected from the group consisting of $C_1$-$C_{10}$ alkyl and aryl;

$R_{o1}$, $R_{o2}$, $R_{m1}$, $R_{m2}$ and $R_p$ are each selected from the group consisting of hydrogen, $C_1$-$C_{20}$ alkyl, $C_1$-$C_{20}$ heteroalkyl, $C_1$-$C_{20}$ alkoxy, aryl, aryloxy, heteroaryl, heterocycloalkyl, disulfide, carbonate, isocyanate, carbodiimide, carboalkoxy, carbamate and halogen, thioether, ketone, aldehyde, ester, ether, amine, amide, nitro, carboxylic acid, the non-hydrogen groups optionally substituted with one or more moieties selected from the group consisting of $C_1$-$C_{20}$ alkyl, $C_1$-$C_{20}$ alkoxy and aryl, wherein $R_{o1}$, $R_{o2}$, $R_{m1}$, $R_{m2}$ and $R_p$ can be joined to form a fused cyclic aliphatic or aromatic ring optionally substituted with one or more moieties selected from the group consisting of $C_1$-$C_{20}$ alkyl, $C_1$-$C_{20}$ heteroalkyl, $C_1$-$C_{20}$ alkoxy, aryl, aryloxy, heteroaryl, heterocycloalkyl, disulfide, carbonate, isocyanate, carbodiimide, carboalkoxy, carbamate and halogen, thioether, ketone, aldehyde, ester, ether, amine, amide, nitro, carboxylic acid, the non-hydrogen groups optionally substituted with one or more moieties selected from the group consisting of $C_1$-$C_{20}$ alkyl, $C_1$-$C_{20}$ alkoxy and aryl.

Preferably the substituents $S_1$ to $S_4$ are selected from the group consisting of hydrogen, amino, substituted or unsubstituted mono- and dialkylamino, $C_1$-$C_{20}$ alkyl, thioalkyl, aryl and aryloxy.

More preferably, the substituents $S_1$ to $S_4$ are selected from the group consisting of hydrogen, methoxy, methylthio, amino, dimethylamino, trifluoromethyl, trifluoromethoxy, t-butyl, phenyl, phenoxy, chloro, bromo, piperidinyl, 1-pyrrolidino, 4-tert-butylphenoxy and 2-pyridyl.

Preferably, $R_{o1}$, $R_{o2}$, $R_{m1}$, $R_{m2}$ and $R_p$ are selected from the group consisting of hydrogen, methyl, isopropyl, t-butyl, methoxy, dimethylamino and nitro.

Specific examples of such Schiff base ligands of the above mentioned general formula wherein B is hydrogen, A is

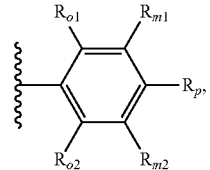

and $S_1$ to $S_4$ and $R_{o1}$, $R_{o2}$, $R_{m1}$, $R_{m2}$ and $R_p$ are as defined below:

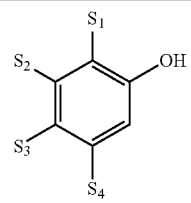 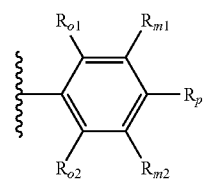

| Compound No. | $S^1$ | $S^2$ | $S^3$ | $S^4$ | $R_{o1}$ | $R_{o2}$ | $R_{m1}$ | $R_{m2}$ | $R_p$ |
|---|---|---|---|---|---|---|---|---|---|
| 1 | H | H | H | H | —CH$_3$ | H | H | H | H |
| 2 | H | H | OCH$_3$ | H | —CH$_3$ | H | H | H | H |
| 3 | H | OCH$_3$ | H | H | —CH$_3$ | H | H | H | H |
| 4 | H | H | OCH$_3$ | H | H | H | H | H | —$^t$But |
| 5 | H | OCH$_3$ | H | H | H | H | H | H | —$^t$But |

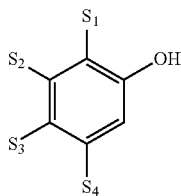 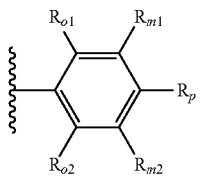

| Compound No. | $S^1$ | $S^2$ | $S^3$ | $S^4$ | $R_{o1}$ | $R_{o2}$ | $R_{m1}$ | $R_{m2}$ | $R_p$ |
|---|---|---|---|---|---|---|---|---|---|
| 6 | —$^t$But | H | —$^t$But | H | —$CH_3$ | H | H | H | H |
| 7 | —$^t$But | H | —$^t$But | H | H | H | H | H | —$^t$But |
| 8 | H | —$^t$But | H | H | $CH_3$ | H | H | H | H |
| 9 | H | —$^t$But | H | H | H | H | H | H | —$^t$But |
| 10 | H | H | H | H | H | H | Br | H | H |
| 11 | H | H | H | H | H | H | H | H | —$^t$But |
| 12 | H | $OCH_3$ | H | H | H | H | H | H | $N(CH_3)_2$ |
| 13 | H | H | $OCH_3$ | H | —$CH_3$ | —$CH_3$ | H | H | H |
| 14 | H | $OCH_3$ | H | H | —$CH_3$ | —$CH_3$ | H | H | H |

The catalytic complex according to the present invention further comprises a nucleophilic carbene ligand ligated to the ruthenium or osmium metal.

Suitable nucleophilic carbene ligands are described in applicant's European patent 1 468 004.

Preferably, the nucleophilic carbene ligand is a substituted or unsubstituted, saturated or unsaturated 1,3 diheteroatomic cyclic compound, wherein the heteroatoms are nitrogen atoms.

Such a 1,3 diheteroatomic cyclic compound may have the formula wherein

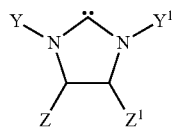

Y and $Y^1$ are independently selected from the group consisting of hydrogen, $C_1$-$C_{20}$ alkyl, $C_2$-$C_{20}$ alkenyl, $C_2$-$C_{20}$ alkynyl, $C_2$-$C_{20}$ alkoxycarbonyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, or aryloxy, each Y and $Y^1$ optionally being substituted with $C_1$-$C_5$ alkyl, halogen, $C_1$-$C_6$ alkoxy, or with a phenyl group substituted with halogen, $C_1$-$C_5$ alkyl or $C_1$-$C_5$ alkoxy and;

Z and $Z^1$ are independently selected from the group consisting of hydrogen, $C_1$-$C_{20}$ alkyl, $C_2$-$C_{20}$ alkenyl, $C_2$-$C_{20}$ alkynyl, $C_2$-$C_{20}$ alkoxycarbonyl, aryl, $C_1$-$C_{20}$ carboxylate, $C_1$-$C_{20}$ alkoxy, $C_2$-$C_{20}$ alkenyloxy, $C_2$-$C_{25}$ alkynyloxy, or aryloxy, each Z and $Z^1$ optionally being substituted with $C_1$-$C_5$ alkyl, halogen, $C_1$-$C_6$ alkoxy, or with a phenyl group substituted with halogen, $C_1$-$C_5$ alkyl or $C_1$-$C_5$ alkoxy, and wherein the ring can be optionally aromatic by introduction of a further double bond in the ring.

Preferably, the nucleophilic carbene ligand is SIMES or IMES and most preferably the nucleophilic carbene ligand is SIMES.

The catalytic complex according to the present invention further comprises a carbon-containing ligand ligated to the ruthenium or osmium metal. This carbon-containing ligand is selected from the group consisting of substituted or unsubstituted alkylidene, vinylidene or indenylidene ligands.

Such alkylidene, vinylidene or indenylidene ligands are described, for example, in WO 00/15339.

Substituents for these ligands are selected from the group consisting of $C_1$-$C_{10}$ alkyl, $C_2$-$C_{20}$ alkynyl, $C_1$-$C_{20}$ alkoxy, $C_2$-$C_{20}$ alkoxycarbonyl and aryl.

Most preferably the carbon-containing ligand is a phenyl-indenylidene ligand.

Suitable carbon-containing ligands are also described in applicant's European patent 1 468 004.

A preferred family of catalytic complexes according to the present invention has the formula

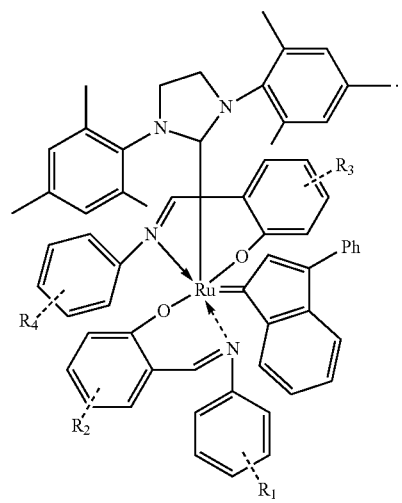

wherein $R_1$, $R_2$, $R_3$ and $R_4$ are independently selected from the group consisting of hydrogen, halogen, $C_1$-$C_{20}$ alkyl, $C_2$-$C_{20}$ alkenyl, $C_2$-$C_{20}$ alkynyl, $C_2$-$C_{20}$ alkoxycarbonyl, aryl, $C_1$-$C_{20}$ carboxylate, alkoxy, $C_2$-$C_{20}$ alkenyloxy, $C_{20}$ alkynyloxy, aryloxy, $C_1$-$C_{20}$ alkylthio, $C_1$-$C_{20}$ alkylsulfonyl, $C_1$-$C_{20}$ alkyl-sulfinyl, and wherein each of $R_1$, $R_2$ $R_3$ and $R_4$ can be substituted with $C_1$-$C_5$ alkyl, halogen, $C_1$-$C_{10}$ alkoxy, or with a aryl group substituted with $C_1$-$C_5$ alkyl, $C_1$-$C_5$ aryloxy, halogen or with a functional group.

A particularly preferred complex according to the present invention has the formula

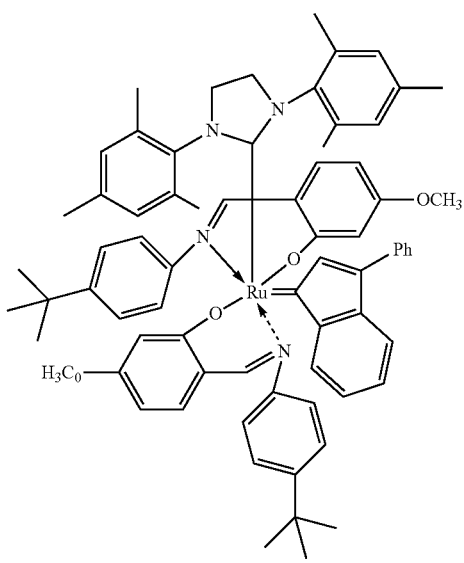

The catalytic complex of the present invention can be used as such or in the form of a supported catalyst comprising the catalytic complex and a carrier.

This carrier may be selected from the group consisting of porous inorganic solids, such as amorphous or paracrystalline materials, crystalline molecular sieves and modified layered materials including one or more inorganic oxides and organic polymers.

The catalytic complex is prepared by a process which comprises the step of reacting a ruthenium or osmium catalyst precursor consisting of:
a. a metal atom selected from the group consisting of ruthenium and osmium;
b. two anionic ligands;
c. a nucleophilic carbene ligand ligated to said metal;
d. a carbon-containing ligand ligated to said metal, wherein said carbon-containing ligand is a substituted or unsubstituted alkylidene, vinylidene or indenylidene ligand; and
e. a neutral ligand
or a ruthenium or osmium catalyst precursor consisting of:
a. a metal atom selected from the group consisting of ruthenium and osmium;
b. one anionic ligand;
c. one bidentate Schiff base ligand comprising an imino group and being coordinated to the metal, in addition to the nitrogen atom of said imino group, through at least one further heteroatom selected from the group consisting of oxygen, sulphur and selenium ligated to said metal;
d. a nucleophilic carbene ligand ligated to said metal; and
e. a carbon-containing ligand ligated to said metal, wherein said carbon-containing ligand is a substituted or unsubstituted alkylidene, vinylidene or indenylidene ligand;
with 1.0 to 3.0 equivalents of a bidentate Schiff base ligand in a non polar solvent and in the presence of a weak base.

Suitable anionic ligands for use in the present invention include anionic ligands selected from the group consisting of $C_{1-20}$ alkyl, $C_{1-20}$ alkenyl, $C_{1-20}$ alkynyl, $C_{1-20}$ carboxylate, $C_{1-20}$ alkoxy, $C_{1-20}$ alkenyloxy, $C_{1-20}$ alkynyloxy, aryl, aryloxy, $C_{1-20}$ alkoxycarbonyl, $C_{1-8}$ alkylthio, $C_{1-20}$ alkylsulfonyl, $C_{1-20}$ alkylsulfinyl, $C_{1-20}$ alkyl-sulfonate, arylsulfonate, $C_{1-20}$ alkylphosphonate, arylphosphonate, $C_{1-20}$ alkylammonium, arylammonium, halogen atoms and cyano. Preferably, the anionic ligands are chloride ligands.

The neutral ligand is preferably a phosphine of the formula $PR^3R^4R^5$ where $R^3$ is a secondary alkyl or cycloalkyl, and each of $R^4$ and $R^5$ is an aryl, $C_1$-$C_{10}$ primary alkyl, secondary alkyl, or cycloalkyl, each independent of the other. More preferably, the neutral ligand is either $P(cyclohexyl)_3$, $P(cyclopentyl)_3$, $P(isopropyl)_3$, or $P(phenyl)_3$.

As the catalytic complex according to the present invention and the compounds used in the process for the preparation thereof are sensitive to air, moisture and impurities, it should be made sure that the starting materials, the reagents and solvents used contain no impurities and are well-dried.

Suitable weak bases for use in the process according to the present invention have a $pK_b$ value in the range of 3.5 to 7. Examples of suitable bases for use in the present invention include $Li_2CO_3$, $Na_2CO_3$, $K_2CO_3$, $CuCO_3$ and $Ag_2CO_3$. $Ag_2CO_3$ having a $pK_b$ value of 3.68 is particularly preferred.

Further examples of the weak base used in the process of the present invention include carboxylates.

For the preparation of the catalytic complex according to the present invention, the catalyst precursor, the Schiff base ligand and the weak base, for example $Ag_2CO_3$ are preferably pre-mixed and then a suitable nonpolar solvent which does not react with any components of the pre-mixture, is added. In the present invention, aprotic solvents which do not possess any acidic protons having a dielectric constant above 3 are preferably used.

Generally, the dielectric constant of the solvent provides a rough measure of a solvent's polarity. Solvents with a dielectric constant of less than 15 are generally considered nonpolar. Technically, the dielectric constant measures the solvent's ability to reduce the field strength of the electric field surrounding a charged particle immersed in it. Examples are given in Table 1 below:

TABLE 1

| solvent | dielectric constant[1] |
|---|---|
| hexane | 1.89 at 20° C. |
| tetrahydrofuran | 7.52 at 25° C. |
| $CH_2Cl_2$ | 8.93 at 25° C. |
| acetone | 21.01 at 20° C. |
| chloroform | 4.81 at 20° C. |
| toluene | 2.38 at 23° C. |
| benzene | 2.28 at 23° C. |
| diethyl ether | 4.34 at 25° C. |

[1]Solvent Physical Properties. Sigma-Aldrich. Retrieved on 23 May 2007.

As mentioned above, the preferred solvent for use in the present invention has a dielectric constant above 3 and such solvents include tetrahydrofuran, methylenedichloride, chloroform and diethylether.

Most preferably, tetrahydrofuran is used as the nonpolar solvent.

The reaction mixture is then heated and stirred. In general, the reaction is carried out at a temperature in the range of 20° C. to the boiling point of the nonpolar solvent used, preferably in the range of 40° C. to 60° C., particularly preferred at about 40° C.

In general, the reaction time is 2 to 72 h.

After the reaction has been completed, the reaction mixture is cooled to about 0° C. to remove any by-products formed by filtration. Subsequently, the solvent is removed by evaporation, usually under reduced pressure.

The amount of weak base used in the process according to the present invention is generally within a range of 0.5 to 2.0 equivalents.

Preferably, the weak base is used in an amount of 0.5 to 1 equivalents, more preferably about 0.6 equivalents relative to the amount of the catalyst precursor when the precursor comprises one anionic ligand and one bidentate Schiff base ligand.

When the precursor comprises two anionic ligands, the weak base is preferably used in an amount of 1.0 to 2.0 equivalents, preferably about 1.1 equivalents relative to the amount of the catalyst precursor.

The amount of the Schiff base ligand used in the process according to the present invention is generally within a range of 1.0 to 3.0 equivalents, preferably 1.0 to 1.5 equivalents and particularly preferred about 1.1 equivalents relative to the amount of the catalyst precursor when the precursor comprises one Schiff base ligand and 2.0 to 2.5 equivalents and particularly preferred about 2.1 equivalents relative to the amount of the catalyst precursor when the precursor comprises two anionic ligands.

Optimum yields of the catalyst of the present invention are achieved when 1 equivalent of the catalyst precursor is reacted with 2.1 equivalents of the Schiff base ligand in the presence of 1.1 equivalents of the weak base, preferably $Ag_2CO_3$, when the precursor comprises two anionic ligands.

Optimum yields of the catalyst of the present invention are achieved when 1 equivalent of the catalyst precursor is reacted with 1.1 equivalents of the Schiff base ligand in the presence of 0.6 equivalents of the weak base, preferably $Ag_2CO_3$, when the precursor comprises one anionic ligand and one Schiff base ligand.

The catalytic complex according to the present invention exhibits a superior latency in the ring opening metathesis polymerisation reaction of dicyclopentadiene (DCPD) compared to ruthenium catalysts of the state of the art. Furthermore, the catalyst according to the present invention is inactive at room temperature and even after heating to 200° C. as demonstrated by DSC measurements. Moreover, the catalyst according to the present invention can be activated with a lower amount of Lewis or Bronsted acid than prior art catalysts.

The present invention is described in more detail in the following examples wherein manipulations of oxygen and moisture-sensitive materials were performed using Schlenck techniques under an Argon atmosphere. THF has been employed as an exemplary solvent.

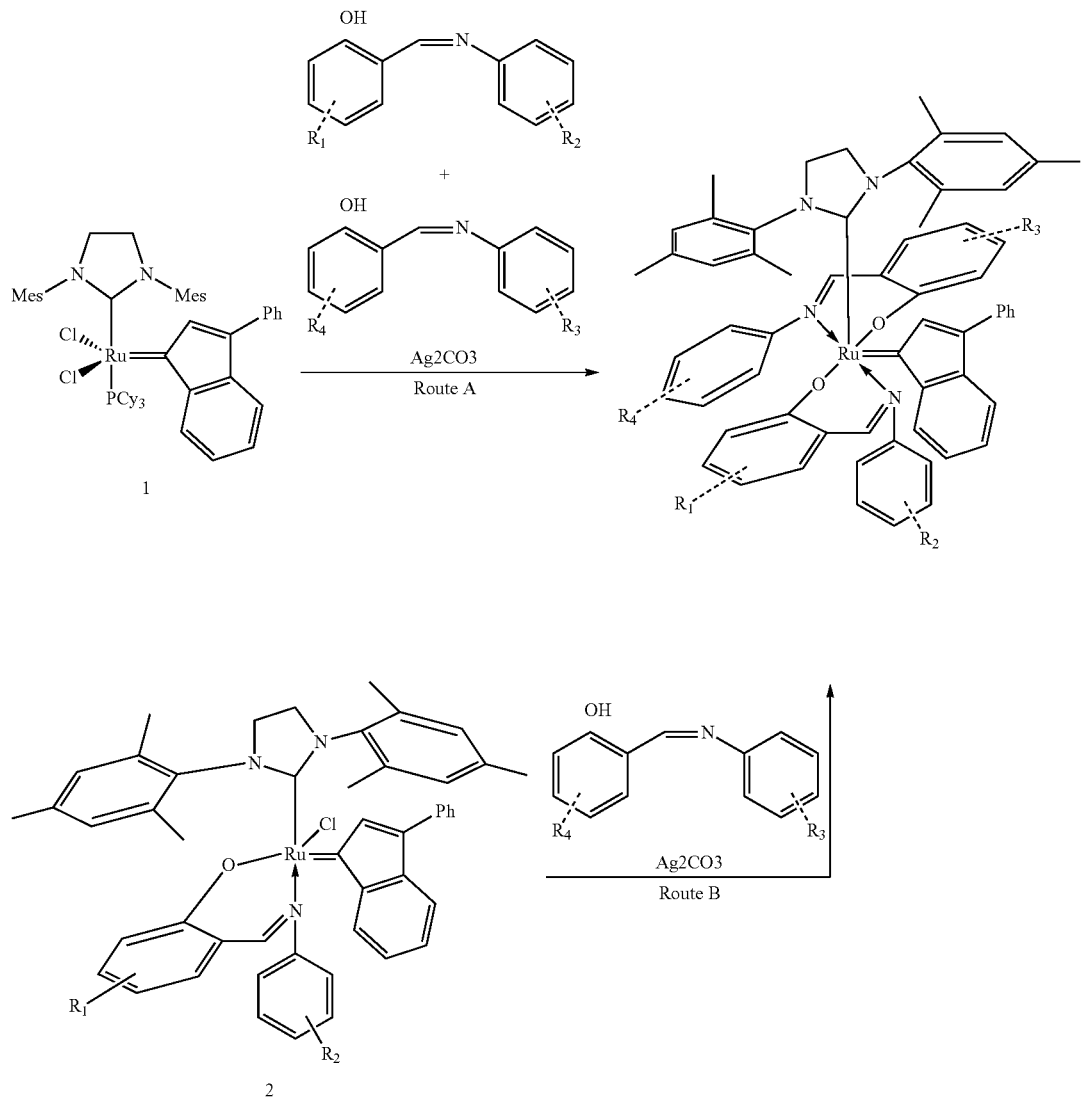

Scheme 3. The synthesis of bis-salicylaldimine catalysts

General Procedure for the Preparation of Phenylindenylidene-Schiff Base-Ruthenium Catalytic Complexes (Scheme 3).

The stoichiometric amounts of phenylindenylidene catalyst precursor 1 (Scheme 3, Route A,), or mono-Schiff base precursors 2 (Scheme 3, Route B), the corresponding Schiff base ligand, silver(I) carbonate, were added to a Schlenk flask (50-250 ml). The flask was evacuated and backfilled with argon. Dry THF (20 ml) was then transferred to the Schlenk flask (still under argon) and stirred for a period of 6-72 h. The reaction mixture was cooled at 0° C. whereas the white precipitate of PCy3AgCl (by-product) was removed by filtration. The filtrate was collected in a Schlenk flask (250 ml), and the solvent was removed by evaporation under reduced pressure. The crude product was suspended in hexane, mixed well and filtrate. The final product was dried under reduced pressure.

Complex 3. Route A. Phenylindenylidene catalyst -precursor 1 (Scheme 3) (0.54 mmol), 2-[(4-$^{tert}$butylphenylimino) methyl]-4-methoxyphenol (1.134 mmol), silver(I) carbonate (0.594 mmol), and THF (10 ml) were reacted as described above for 72 h at room temperature. The reaction mixture was investigated on $^1$H and 31 P NMR, which revealed quantitative transformation to complex 3.

Complex 3. Route B. Ruthenium[1,3-Bis(2,4,6-trimethylphenyl)-2-imidazolidi-nylidene]-[2-[[(4-$^{tert}$butylphenylimino)methyl]-4-methoxyphenolyl]-[3-phenyl-1H-inden-1-ylidene] ruthenium(II) chloride (0.54 mmol), 2-[(4-$^{tert}$butylphenylimino)-methyl]-4-methoxyphenol (0.594 mmol), silver(I) carbonate (0.324 mmol), and THF (10 ml) were reacted as described above for 24 h at room temperature. The reaction mixture was investigated on $^1$H and $^{31}$P NMR, which revealed quantitative transformation to complex 3.

Complex 4. Route A. Phenylindenylidene catalyst precursor 1 (Scheme 3) (0.54 mmol), 2-[(4-$^{tert}$butylphenylimino) methyl]-5-methoxyphenol (1.134 mmol), silver(I) carbonate (0.594 mmol), and THF (10 ml) were reacted as described above for 72 h at room temperature. The reaction mixture was investigated on $^1$H and $^{31}$P NMR, which revealed quantitative transformation to complex 4.

Complex 4. Route B. Ruthenium[1,3-Bis(2,4,6-trimethylphenyl)-2-imidazolidinylidene]-[2-[[(4-tertbutylphenylimino)methyl]-5-methoxyphenolyl[-]3-phenyl-1H-inden-1-ylidene] ruthenium(II) chloride (0.54mmol), 2-[(4-$^{tert}$butylphenylimino)-methyl]-5-methoxyphenol (0.594 mmol), silver(I) carbonate (0.324mmol), and THF (10 ml) were reacted as described above for 72 h at room temperature. The reaction mixture was investigated on $^1$H and $^{31}$P NMR, which revealed quantitative transformation to complex 4.

Complex 5. Route A. Phenylindenylidene catalyst precursor 1 (Scheme 3) (0.54 mmol)2-[(4-methylphenylimino)methyl]-5-methoxyphenol (1.134mmol), silver(I) carbonate (0.594 mmol), and THF (10 ml) were reacted as described above for 72 h at room temperature. The reaction mixture was investigated on $^1$H and 31P NMR, which revealed quantitative transformation to complex 5.

Complex 5. Route B. Ruthenium[1,3-Bis(2,4,6-trimethylphenyl)-2-imidazolidi-nylidene]-[2-[[(4-methylphenylimino)methyl]-5-methoxyphenolyl]-[3-phenyl-1H-inden-1-ylidene] ruthenium(II) chloride (0.54mmol), 2-[(4-methylphenylimino)-methyl]-5-methoxyphenol (0.594 mmol), silver(I) carbonate (0.324 mmol), and THF (10 ml) were reacted as described above for 24 h at room temperature. The reaction mixture was investigated on $^1$H and $^{31}$P NMR, which revealed quantitative transformation to complex 6.

Complex 6. Route A. Phenylindenylidene catalyst precursor 1 (Scheme 3) (0.54 mmol), 2-[(4-methylphenylimino) methyl]-5-methoxyphenol (0.54 mmol), silver(I) carbonate (0.594 mmol), and THF (10 ml) were reacted as described above for 72 h at room temperature and 2-[(4-methylphenylimino)methyl]-4-methoxyphenol (0.594 mmol) was added. The resulting mixture was reacting for additional 48 h. The reaction mixture was investigated on $^1$H and $^{31}$P NMR, which revealed quantitative transformation to complex 6.

Complex 6. Route B. Ruthenium[1,3-Bis(2,4,6-trimethylphenyl)-2-imidazolidinylidene]-[2-[[(4-methylphenylimino)methyl]-5-methoxyphenolyl]-[3-phenyl-1H-inden-1-ylidene] ruthenium(II) chloride (0.54mmol), 2-[(4-methylphenylimino)-methyl]-4-methoxyphenol (0.594 mmol), silver(I) carbonate (0.324 mmol), and THF (10 ml) were reacted as described above for 24 h at room temperature. The reaction mixture was investigated on $^1$H and $^{31}$P NMR, which revealed quantitative transformation to complex 6.

Complex 7. Route A. Phenylindenylidene catalyst precursor 1 (Scheme 3) (0.54 mmol), 2-[(4-$^{iso}$propylphenylimino) methyl]-5-methoxyphenol (1.134 mmol), silver(I) carbonate (0.594 mmol), and THF (10 ml) were reacted as described above for 72 h at room temperature. The reaction mixture was investigated on $^1$H and $^{31}$P NMR, which revealed quantitative transformation to complex 7.

Complex 7. Route B. Ruthenium[1,3-Bis(2,4,6-trimethylphenyl)-2-imidazolidi-nylidene]-[2-[[(4-$^{iso}$propyllphenylimino)methyl]-5-methoxyphenolyl]-[3-phenyl-1H-inden-1-ylidene] ruthenium(II) chloride (0.54 mmol), 2-[(4-propyllphenyliminm)-methyl]-5-methoxyphenol (0.594 mmol), silver(I) carbonate (0.324 mmol), and THF (10 ml) were reacted as described above for 24 h at room temperature. The reaction mixture was investigated on $^1$H and $^{31}$P NMR, which revealed quantitative transformation to complex 7.

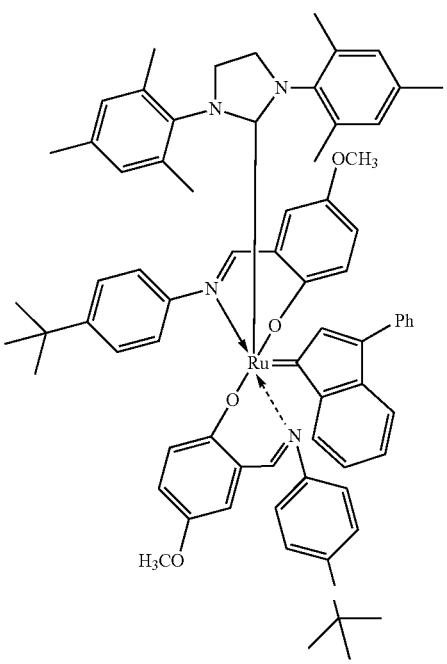

3

-continued
4
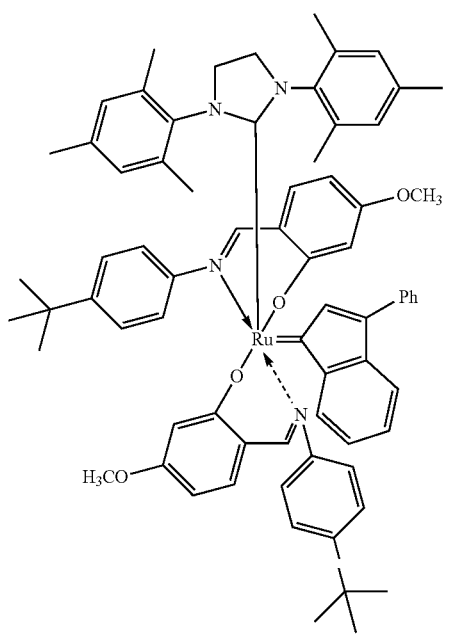
5
6
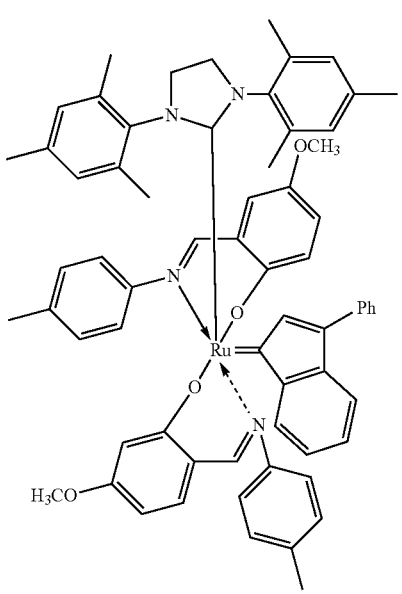
7
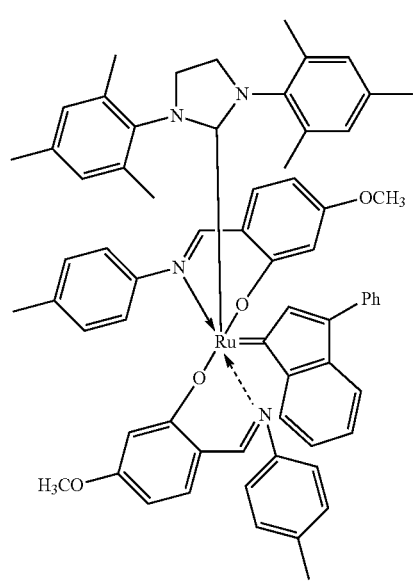
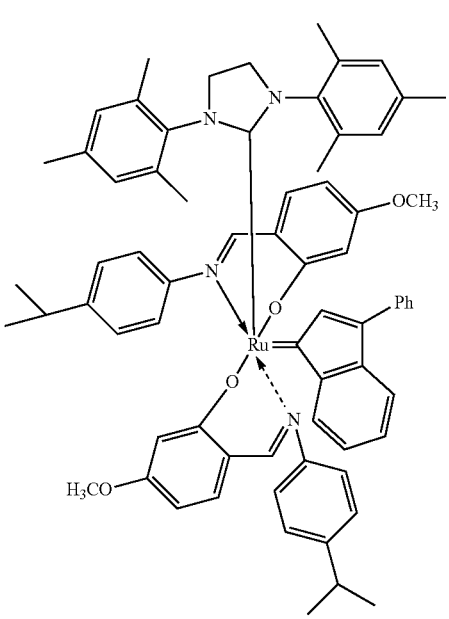
Catalyst Performance
The ruthenium catalytic complex (4) according to the present invention as shown above has been tested in ROMP of DCPD. A ruthenium catalyst (2a) comprising only one bidentate Schiff base ligand has been used as a reference catalyst:

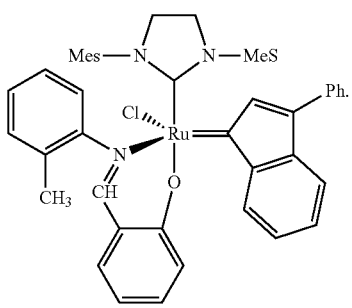

(2a)

The results achieved are presented in Table 2 below.

TABLE 2

Performance of the catalysts in ROMP of DCPD (Conditions: 80 g DCPD)

| Catalyst | Latency | Cocatalyst | Cl/Ru | DCPD/Ru | $T_{max}$ | $T_{g1}$ | $T_{g2}$ |
|---|---|---|---|---|---|---|---|
| 4 | good | PhSiCl$_3$ | 2 | 30 000 | 217° C. | 171° C. | 178° C. |
| 2a* | good | PhSiCl$_3$ | 45 | 30 000 | 215° C. | 156° C. | 169° C. |

*for reference purpose

The salicylaldimine ligand of the reference catalyst (2a) bears a substituent in ortho-position in the aniline moiety and ruthenium catalysts of this type having a salicylaldimine ligand with such an ortho-substituent exhibit a good latency in ring opening metathesis polymerisation reactions of dicyclopentadiene.

In spite of lacking such a substituent, the ruthenium catalytic complex 4 according to the present invention has been found to be an exceptional latent catalyst in the ROMP of DCPD (catalyst/monomer ratio of 1:15000), inactive at room temperature and even after heating to above 200° C. as proven by DSC measurements. The stability of the bis-substituted catalytic complex 4 of the present invention is superior to that of the more reactive mono-substituted analog and as good as that of the reference catalyst (2a) (cf. Table 2). The improved stability of the ruthenium catalyst 4 according to the present invention in the ROMP of DCPD is in part due to the increase in sterical hindrance around the ruthenium center.

Upon its chemical activation, the bis-salicylaldimine catalytic complex 4 according to the present invention demonstrates an increased initiation compared to the reference catalyst (2a) because it requires only less than 1 equivalent of PhSiCl$_3$ to generate a highly active system. When the ROMP of DCPD is catalyzed by the chemically activated complex 2a under the same conditions (less than 1 equivalent of PhSiCl$_3$) low catalytic activity was observed. Even after chemical activation using 45 equivalents of PhSiCl$_3$ the reference catalyst (2a) still exhibits a slower initiation compared to the ruthenium complex 4 according to the present invention.

Thus, after its activation the ruthenium complex 4 according to the present invention significantly outperforms the reference catalyst (2a) giving a polymer having excellent properties such as glass transition temperatures at 171° C. and 178° C., which are superior to those obtained by using other latent catalysts.

The invention claimed is:

1. A process for the preparation of a catalytic complex consisting of:
    a. a metal atom selected from the group consisting of ruthenium and osmium;
    b. two bidentate Schiff base ligands comprising an imino group and being coordinated to the metal, in addition to the nitrogen atom of said imino group, through at least one further heteroatom selected from the group consisting of oxygen, sulphur and selenium ligated to said metal;
    c. a nucleophilic carbene ligand ligated to said metal; and
    d. a carbon-containing ligand ligated to said metal, wherein said carbon-containing ligand is a substituted or unsubstituted alkylidene, vinylidene or indenylidene ligand;
    which comprises the step of reacting a ruthenium or osmium catalyst precursor consisting of:
    a. a metal atom selected from the group consisting of ruthenium and osmium;
    b. two anionic ligands;
    c. a nucleophilic carbene ligand ligated to said metal;
    d. a carbon-containing ligand ligated to said metal, wherein said carbon-containing ligand is a substituted or unsubstituted alkylidene, vinylidene or indenylidene ligand; and
    e. a neutral ligand or a ruthenium or osmium catalyst precursor consisting of:
       a. a metal atom selected from the group consisting of ruthenium and osmium;
       b. one anionic ligand;
       c. one bidentate Schiff base ligand comprising an imino group and being coordinated to the metal, in addition to the nitrogen atom of said imino group, through at least one further heteroatom selected from the group consisting of oxygen, sulphur and selenium ligated to said metal;
       d. a nucleophilic carbene ligand ligated to said metal; and
       e. a carbon-containing ligand ligated to said metal, wherein said carbon-containing ligand is a substituted or unsubstituted alkylidene, vinylidene or indenylidene ligand;
    with 1.0 to 3.0 equivalents of a bidentate Schiff base ligand in a non polar solvent and in the presence of a weak base.

2. The process of claim 1 wherein the two anionic ligands of said catalyst precursor are chloride ligands and the neutral ligand is a phosphine ligand.

3. The process of claim 1 wherein the catalyst precursor comprises a bidentate Schiff base ligand comprising an imino group and being coordinated to the metal, in addition to the nitrogen atom of said imino group, through at least one further heteroatom selected from the group consisting of oxygen, sulphur and selenium ligated to said metal, and a chloride as anionic ligand.

4. The process of claim 1 wherein the weak base is Ag$_2$CO$_3$.

5. The process of claim 2 wherein the weak base is used in an amount of 1 to 2 equivalents, relative to the amount of the catalyst precursor.

6. The process of claim 3 wherein the weak base is used in an amount of 0.5 to 1 equivalents, relative to the amount of the catalyst precursor when said precursor comprises one anionic ligand and one bidentate Schiff base ligand.

7. The process of claim 1 wherein the nonpolar solvent is tetrahydrofuran.

8. The process of claim 1 wherein the reaction step is carried out at a temperature within the range of 20° C. to the boiling point of the nonpolar solvent.

9. A catalytic complex obtainable by the process of claim 1.

10. The catalytic complex of claim 9 wherein the nucleophilic carbene ligand is a substituted or unsubstituted, saturated or unsaturated 1,3 diheteroatomic cyclic compound, wherein the heteroatoms are nitrogen atoms.

11. The catalytic complex of claim 9 wherein the bidentate Schiff base ligand is derived from a compound having the formula:

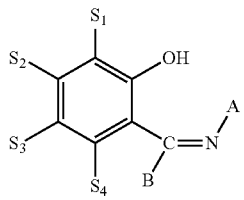

wherein $S_1$ to $S_4$ are substituents which are selected such that the compound has a $pK_a \geqq 6.2$, in the presence of a weak base having a $pK_b$ in the range of 3.5-7.0;

A is

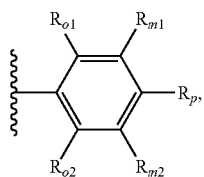

heteroaryl, substituted or unsubstituted alkyl, heteroalkyl or cycloalkyl,

B is hydrogen, $C_1$-$C_{20}$ alkyl, $C_1$-$C_{20}$ heteroalkyl aryl or heteroaryl, wherein each non-hydrogen group may be optionally substituted with one or more moieties selected from the group consisting of $C_1$-$C_{10}$ alkyl and aryl;

$R_{o1}$, $R_{o2}$, $R_{m1}$, $R_{m2}$ and $R_p$ are each selected from the group consisting of hydrogen, $C_1$-$C_{20}$ alkyl, $C_1$-$C_{20}$ heteroalkyl, $C_1$-$C_{20}$ alkoxy, aryl, aryloxy, heteroaryl, heterocycloalkyl, disulfide, carbonate, isocyanate, carbodiimide, carboalkoxy, carbamate and halogen, thioether, ketone, aldehyde, ester, ether, amine, amide, nitro, carboxylic acid, the non-hydrogen groups optionally substituted with one or more moieties selected from the group consisting of $C_1$-$C_{20}$ alkyl, $C_1$-$C_{20}$ alkoxy and aryl, wherein $R_{o1}$, $R_{o2}$, $R_{m1}$, $R_{m2}$ and $R_p$ can be joined to form a fused cyclic aliphatic or aromatic ring optionally substituted with one or more moieties selected from the group consisting of $C_1$-$C_{20}$ alkyl, $C_1$-$C_{20}$ heteroalkyl, $C_1$-$C_{20}$ alkoxy, aryl, aryloxy, heteroaryl, heterocycloalkyl, disulfide, carbonate, isocyanate, carbodiimide, carboalkoxy, carbamate and halogen, thioether, ketone, aldehyde, ester, ether, amine, amide, nitro, carboxylic acid, the non-hydrogen groups optionally substituted with one or more moieties selected from the group consisting of $C_1$-$C_{20}$ alkyl, $C_1$-$C_{20}$ alkoxy and aryl.

12. The catalytic complex of claim 9 wherein the substituents of the carbon-containing ligand are selected from the group consisting of $C_1$-$C_{10}$ alkyl, $C_2$-$C_{20}$ alkynyl, $C_1$-$C_{20}$ alkoxy, $C_2$-$C_{20}$ alkoxycarbonyl, and aryl.

13. The catalytic complex of claim 9 wherein the carbon-containing ligand is phenylindenylidene.

14. The catalytic complex of claim 9 having the formula:

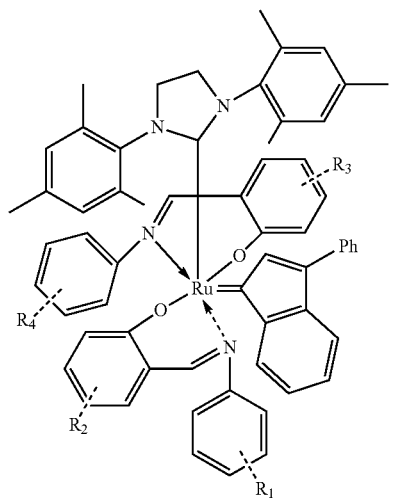

wherein $R_1$, $R_2$, $R_3$ and $R_4$ are independently selected from the group consisting of hydrogen, halogen, $C_1$-$C_{20}$ alkyl, $C_2$-$C_{20}$ alkenyl, $C_2$-$C_{20}$ alkynyl, $C_2$-$C_{20}$ alkoxycarbonyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_1$-$C_{20}$ alkylthio, $C_1$-$C_{20}$ alkylsulfonyl, $C_1$-$C_{20}$ alkylsulfinyl, and wherein each of $R_1$, $R_2$, $R_3$ and $R_4$ can be substituted with $C_1$-$C_5$ alkyl, halogen, $C_1$-$C_{10}$ alkoxy, or with a aryl group substituted with $C_1C_5$ alkyl, $C_1$-$C_5$ aryloxy, halogen or with a functional group.

15. A supported catalyst comprising the catalytic complex of claim 9 and a carrier.

16. The supported catalyst of claim 15 wherein the carrier is selected from the group consisting of porous inorganic solids and organic polymers.

17. A method of olefin metathesis reaction comprising the step of reacting olefins in the presence of the catalytic complex as defined in any one of claims 9 to 14 or the supported catalyst as defined in any one of claims 15 and 16.

18. The method according to claim 17 wherein the olefin metathesis reaction is a ring opening metathesis polymerization.

* * * * *